United States Patent [19]

Gonzalo

[11] Patent Number: 4,627,837
[45] Date of Patent: Dec. 9, 1986

[54] CATHETER DEVICE

[76] Inventor: German Gonzalo, 30 Oaklane Dr., Ottawa, Ill. 61350

[21] Appl. No.: 615,399

[22] Filed: May 30, 1984

[51] Int. Cl.⁴ ............................................. A61M 29/00
[52] U.S. Cl. ..................................... 604/101; 128/328
[58] Field of Search ................ 604/101; 128/325, 328, 128/346, 348.1

[56] References Cited

U.S. PATENT DOCUMENTS

| | | | |
|---|---|---|---|
| 2,936,760 | 5/1960 | Gants | 604/101 |
| 3,046,988 | 7/1962 | Moreau et al. | 604/101 X |
| 4,295,464 | 10/1981 | Shihata | 128/328 |
| 4,469,100 | 9/1984 | Hardwick | 128/328 |

*Primary Examiner*—John D. Yasko
*Attorney, Agent, or Firm*—McDermott, Will & Emery

[57] ABSTRACT

Disclosed is a catheter device equipped at its distal portion with a pair of balloons inflatable from the proximal end of the catheter. One balloon completely covers the distal tip of the catheter to serve, when inflated, as an anchor to retain the catheter in an appropriate ampulla and as a cushion to prevent internal tissue damage. The second balloon serves, when inflated, to remove and dislodge impacted biliary stones. In addition, a separate chamber in the second balloon is available for irrigating and flushing biliary stones and in conjunction with an inflatable balloon adjustably mounted on the catheter can perform cholaniograms. The separate chamber also functions as a hinge allowing the second balloon to inflate proximally, resulting in a heart-shaped structure assuring successful stone removal.

16 Claims, 8 Drawing Figures

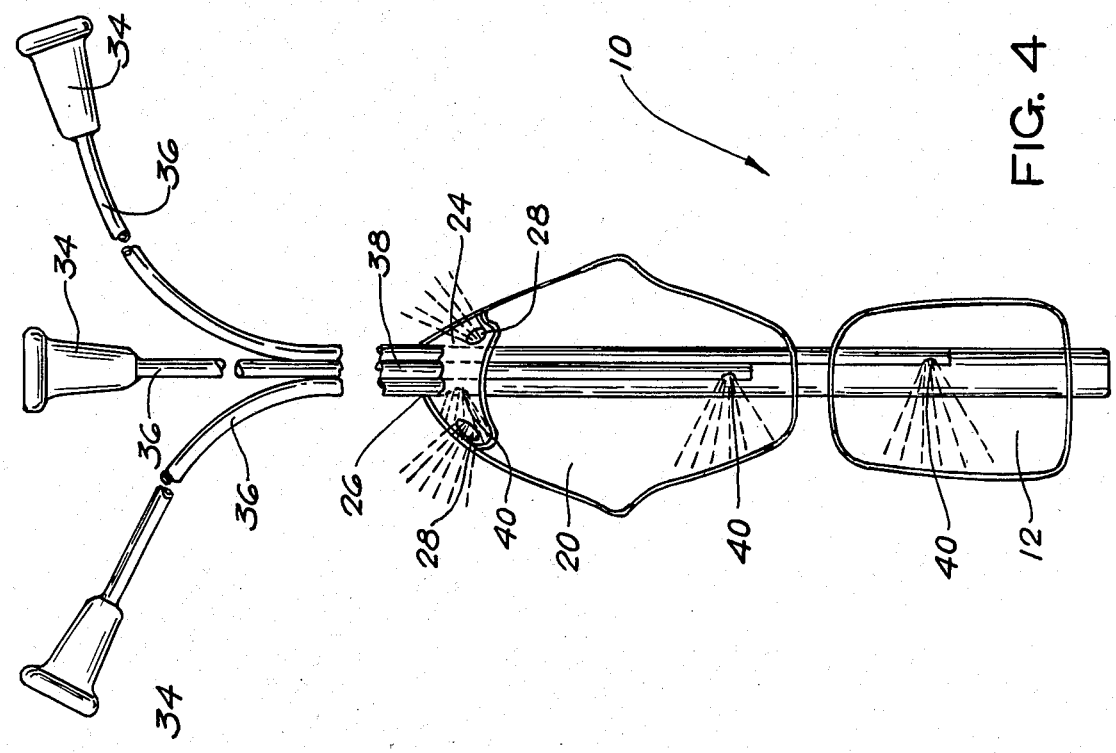
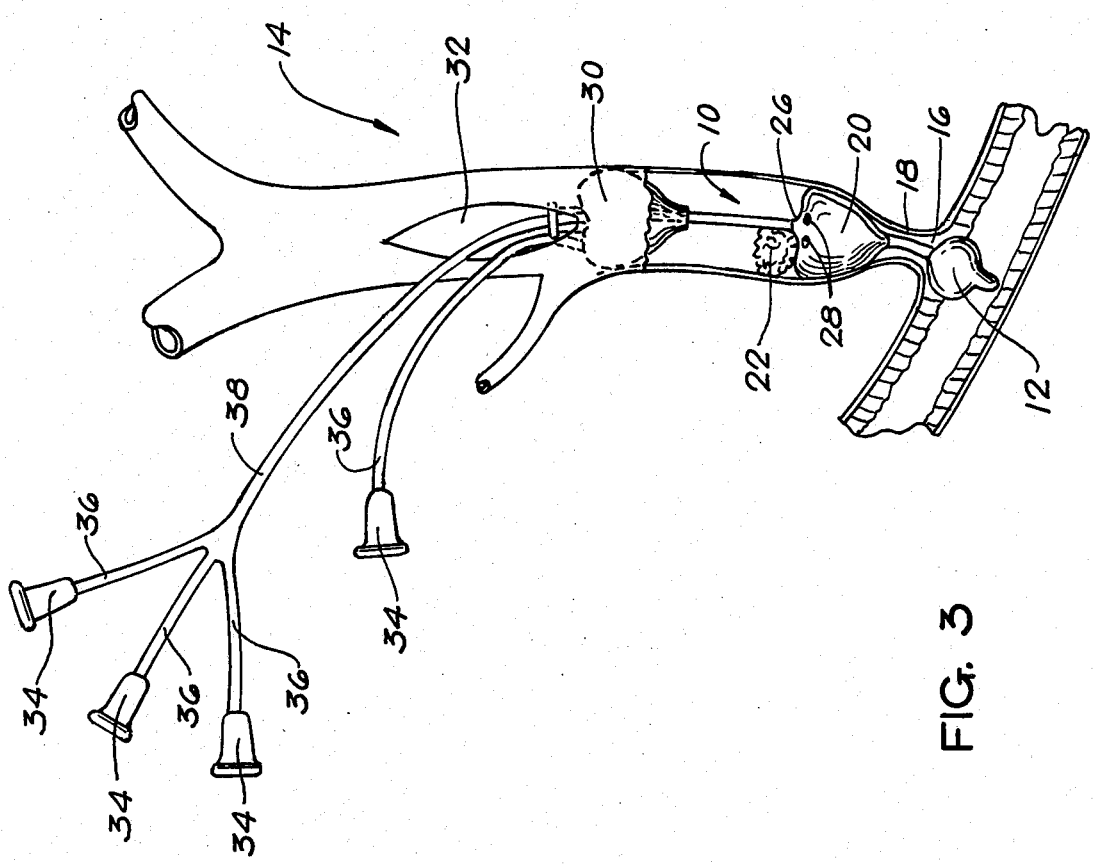

CATHETER DEVICE

BACKGROUND OF THE INVENTION

1. Field of the Invention

The present invention relates to catheters and the like, and has particular reference to a novel construction for a biliary stone removal device which performs functions previously unavailable in such a device.

2. Brief Description of the Background Art

Multichannel catheters now used are generally of similar construction. There will most often be a channel for each inflatable balloon incorporated therein and a large passage for drainage if that is a function of the device. For convenience these channels are usually attached along their length or fitted inside the large channel if appropriate. Occasionally a balloon fitted to a catheter will not be fixed but slides along the device. These balloons may temporarily lock in place when inflated. Channels for sliding balloons are not commonly attached to the catheter device.

SUMMARY OF THE INVENTION

It is an object of this invention to provide a catheter with a balloon that inflates proximally to form a heart-shaped structure.

It is another object of this invention to provide a catheter with a sliding balloon of approximate utility for sealing off choledochotomy sites when positioned and inflated.

It is a specific object of this invention to provide a catheter incorporating an inflatable balloon with an integral chamber for intromitting intralumenous fluids.

It is an object of this device to provide a catheter with an inflatable balloon enveloping the closed distal tip of the catheter cushioning said tip and preventing tissue trauma.

It is a further specific object to provide a catheter with an inflatable balloon that automatically anchors the device in its proper location readying it for immediate use upon inflation.

In a broad embodiment therefor, these objects and others are provided by an improved catheter device. This catheter device is a four-channel catheter having three balloons. Two balloons are integrally mounted in fixed positions at the distal end of the device. The third balloon is of the sliding type such that its position may become fixed, but not permanent, upon inflation and adjustable again upon deflation. The extreme distal balloon envelopes the distal tip of the device. When inflated this balloon serves to anchor the catheter device in an ampulla. This prevents the catheter from being accidentally withdrawn and positions the catheter for use. The second fixed balloon neighbors the first at the distal end of the device. When the inflated first balloon has been pulled into the ampulla of Vater the second balloon is positioned distally of any biliary stone that could be present in the common duct. By inflating this second balloon, deflating the first and withdrawing the device any stones present in the common duct will be removed.

When the catheter is in position with the first balloon placed in the ampulla of Vater and inflated, the sliding balloon may be inserted through the choledochotomy into the common duct. When the sliding balloon is inflated, the separate chamber in the second balloon may be used to exude contrast material into the common duct for a cholangiogram. This can be done either before or after the stone removal procedure to determine if there are stones to remove or if all the stones have been removed. The inflated sliding balloon prevents the contrasting material from leaking out. In addition, the separate chamber in the second balloon may be used to flush biliary stones during the removal procedure, and with the sliding balloon deflated and removed, to flush the common duct of the contrasting material after the cholangiogram procedure.

BRIEF DESCRIPTION OF THE DRAWINGS

FIG. 3 is the catheter described in FIG. 1 wherein said catheter is being prepared for performing a cholangiogram;

FIG. 4 is an enlarged sectional detail of the distal portion of the present invention;

DETAILED DESCRIPTION OF THE INVENTION

Figure 2:
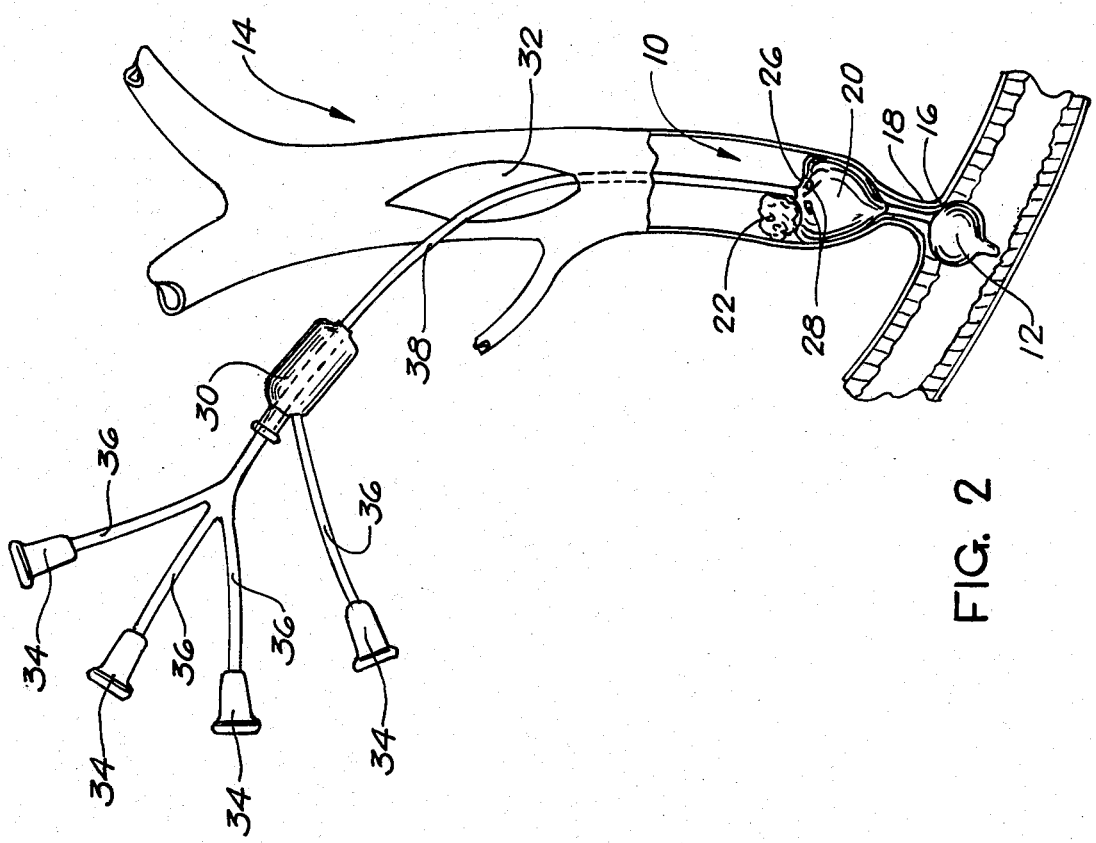
FIG. 2 is the catheter described in FIG. 1 wherein said catheter is being prepared for removing biliary stones from the common duct.
Figure 1:
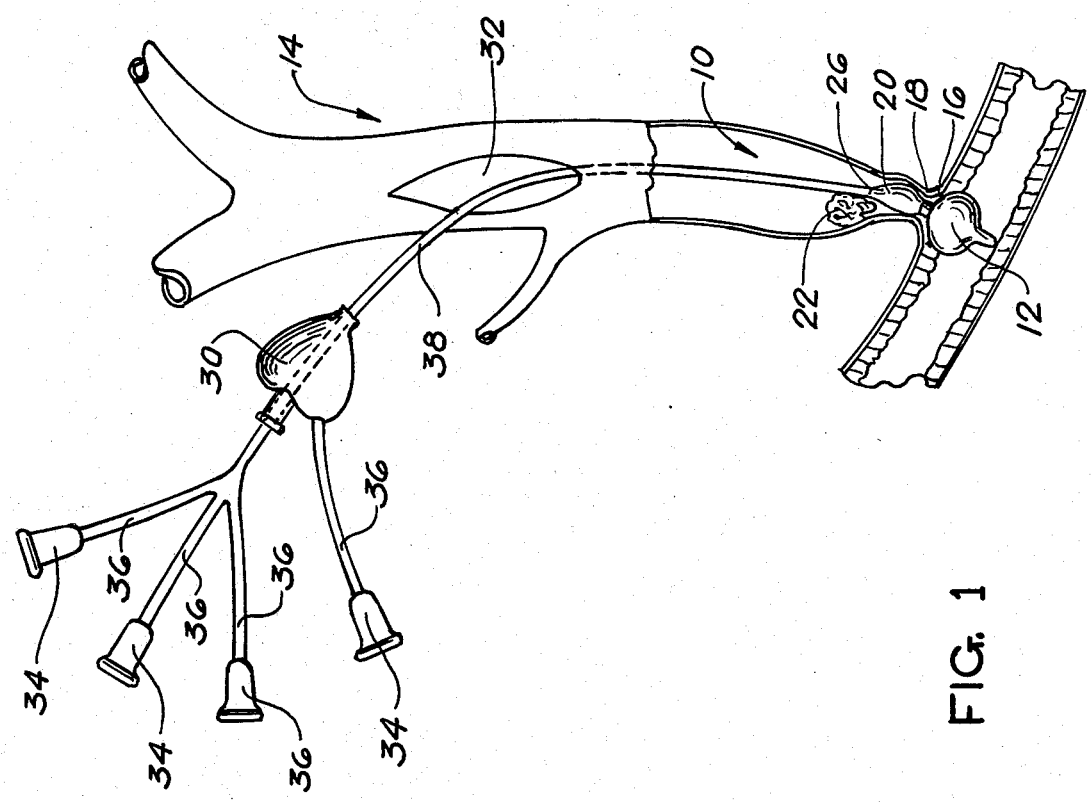
FIG. 1 is a partially schematic illustration of an installed catheter constructed in accordance with the present invention.
Figure 5A:
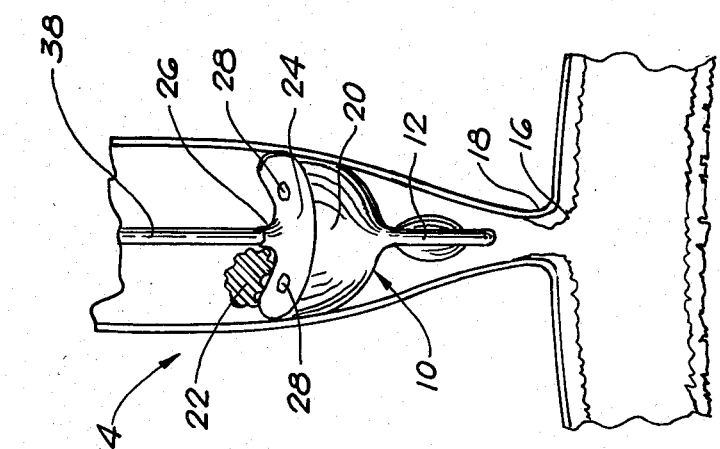
FIG. 5a is an enlarged detail of the distal portion of the catheter described in FIG. 1.
Figure 5B:
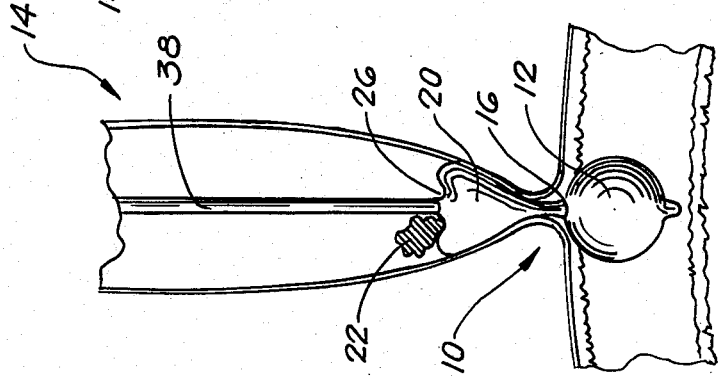
FIG. 5b is an enlarged detail of the distal portion of the catheter described in FIG. 2.
Figure 5C:
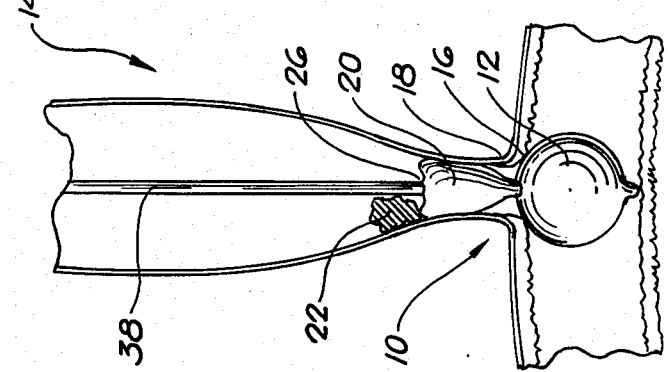
FIG. 5c is the catheter described in FIG. 5b wherein said catheter has been prepared for removing biliary stones from the common duct.
Figure 5D:
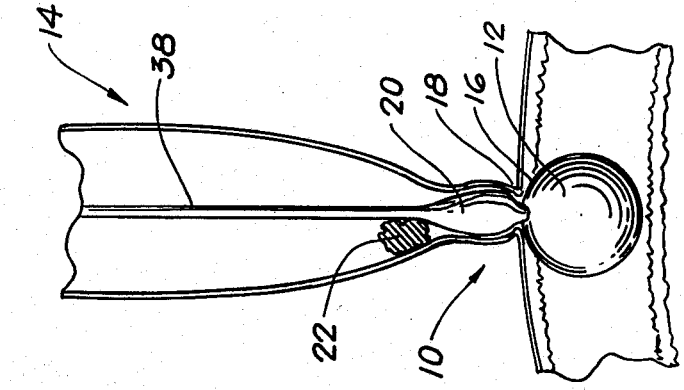
FIG. 5d is the catheter described in FIG. 5b wherein said catheter is removing biliary stones from the common duct.

The catheter device of the present invention, generally designated 10, disclosing its several improvements over the prior art is shown in FIG. 1. According to customary terminology, the portion of the catheter device 10 which remains outside of the common duct for operation by the physician or other clinician is referred to as the proximal end. The end of the catheter 10 which is inserted into the common duct of a patient through a choledochotomy is referred to as the distal end. The catheter device 10 of the present invention includes a flexible main stem or channel 11 connecting the distal and proximal ends and a flexible bulbous portion or balloon 12 mounted on its extreme distal end which is used to secure the catheter device 10 in its proper position. More particularly, referring to FIGS. 1 and 2, the catheter is shown installed in a common duct, generally designated 14, with the distal balloon 12 of the catheter 10 placed in the duodenum 16 and thereafter inflated as can be seen in the drawings. The inflated distal balloon 12 placed in the duodenum 16 anchors the catheter device 10 against the sphincter of Oddi 18. The inflated distal balloon 12 cannot pass through the smaller diameter of the sphincter of Oddi 18. This anchoring prevents accidental removal of the catheter device 10.

In addition, the second balloon 20 which is fixed in a position on the catheter device 10 proximal to the extreme distal balloon 12 is automatically placed proximally to both the ampulla of Vater and the sphincter of Oddi 18. This positioning of the second balloon 20 ensures that the second balloon 20 will be placed distally of any biliary stones 22 present in the common duct 14.

There is incorporated into the proximal end of the second balloon 20 a separate chamber 24. This separate chamber 24 functions as a hinge 26 so that the second balloon 20 assumes a heart or arrow shape upon inflation which seems to generally bias any stone toward the center of the duct when withdrawn. When the second balloon 20 is inflated and the distal balloon 12 deflated the catheter device 10 may be withdrawn thereby forcefully dislodging and removing any stones.

A number of vent holes 28 placed in the separate chamber 24 allow the intromission of intralumenous fluids during the removal of the catheter 10. This flushing of the biliary stones 22 and the heart shaped conformation of the second balloon 20 ensure efficient biliary stone 22 removal.

An additional sliding balloon 30 may be slidably mounted on the catheter device 10 proximally of the second balloon 20. This sliding balloon 30 temporarily locks in place when inflated and releases upon deflation. When the sliding balloon 30 is positioned in the common duct 14 just inside the choledochotomy 32 and inflated a cholangiogram may be performed. The sliding balloon 30 is positioned at a desired location and inflated and a contrasting material is introduced to the common duct 14 by the vent holes 28 in the separate chamber 24 of the second balloon 20. The inflated sliding balloon 30 seals the common duct 14 distally of the choledochotomy 32 preventing leakage of the contrasting material. After the cholangiogram is performed the sliding balloon 30 is deflated and removed. The vent holes 28 in the separate chamber 24 of the second balloon 20 allow the contrasting material to be flushed clear of the common duct 14 if desired.

Fluids passing into the balloons 12, 20 and 30 and the separate chamber 24 are introduced to the proximal end of the catheter device 10 at the entry ports 34. Fluids are transmitted to the balloons 12, 20 and 30 and the separate chamber 24 from the entry ports 34 by catheter channels 36. The catheter channels for the two distal balloons 12 and 20 and the separate chamber 24 come together as an integrated channel 38. This integrated channel 38 passes through the distal end of the catheter device 10. Individual channels 36 are breached when appropriate 40 as the integrated channel 38 passes through the separate chamber 24, the second balloon 20 and the distal balloon 12. The channel 36 connecting the sliding balloon 30 with its entry port 34 is separate from the integrated channel 38 to ensure mobility of the sliding balloon 30.

It should be understood that various modifications within the scope of this invention can be made by one of ordinary skill in the art without departing from the spirit thereof. Therefore, the invention should be defined by the following claims as broadly as the prior art will permit and in view of the specifications if need be.

I claim:

1. A catheter device for use in removing biliary stones, comprising:
   a main channel;
   means for removing biliary stones from the common duct mounted on said channel including an inflatable balloon and means for remotely inflating the same;
   biliary stone removal means for removing biliary stones from the common duct;
   anchoring means for securing the catheter in the common duct; and
   fluid exuding means for flushing biliary stones as they are removed from the common duct, said fluid exuding means being connected to said balloon.

2. The catheter device of claim 1 wherein said biliary stone removal means is proximally mounted on said channel from said anchoring means.

3. The catheter device of claim 2 wherein said anchoring means includes a balloon distally mounted on the main channel of said catheter device and means for inflating said balloon.

4. The catheter device of claim 3 wherein said fluid exuding means includes a separate chamber adjacent said balloon and means for filling same.

5. The catheter device of claim 4 wherein said balloon inflating and chamber filling means includes separate channels adjacent said balloon and means for introducing fluids therein.

6. The catheter device of claim 5 wherein said means for introducing fluids therein comprises separate fluid entry ports proximally mounted on separate channels.

7. The catheter device of claim 6 wherein said separate chamber is proximally incorporated in said biliary stone removal device.

8. The catheter device of claim 7 wherein said biliary stone removal device includes means connecting the proximal end thereof to said main channel whereby inflation of said balloon causes portions thereof to extend proximally of said connecting means.

9. The catheter device of claim 8 wherein said separate chamber is mounted within said balloon and proximally incorporated therein.

10. A catheter device for use in performing cholangiograms, comprising:
    a main stem portion;
    anchoring means mounted on the distal end of said stem for securing the catheter in the common duct;
    sealing means for preventing leakage proximally of said sealing means at the choledochtomy site; and
    fluid exuding means for admitting suitable material to the common duct, said fluid exuding means being located between said anchoring means and said sealing means.

11. The catheter device of claim 10 wherein said anchoring means includes a balloon distally mounted on said stem and means for remotely inflating said balloon.

12. The catheter device of claim 11 wherein said sealing means includes a second inflatable balloon slidably mounted on said stem proximally of said anchoring means and means for inflating said second balloon.

13. The catheter device of claim 12 wherein said fluid exuding means includes a separate chamber mounted between said anchoring means and said sealing means and means for filling said chamber.

14. The catheter device of claim 13 wherein said balloon inflating and chamber filling means includes separate channels adjacent said stem and means for introducing fluids therein.

15. The catheter device of claim 14 wherein said means for introducing fluids therein comprises separate fluid entry ports proximally mounted on said catheter device.

16. A catheter device, comprising:
    (A) A distal section wherein:
    (1) an inflatable balloon provides for securing the device wherein:
    (2) an inflatable balloon is located proximally of said distal balloon for removing biliary stones wherein:

(a) said proximal balloon contains a separate chamber for admitting fluid to the common duct; and (b) said proximal balloon inflates to a heart shape for better removing biliary stones wherein:

(i) said separate chamber is the hinging means for the proximal balloon to assume a heart shape upon inflation.

(B) a middle section wherein:

(1) said middle section contains sealing means for preventing leaks at the choledochotomy site wherein:

(a) said sealing means is an inflatable sliding balloon wherein:

(i) said sliding balloon adjusts proximally and distally when deflated and locks in position when inflated; and (C) a proximal section wherein:

(1) said proximal section contains four entry ports for admitting fluids to said balloons and said separate chamber wherein:

(a) said entry ports lead into channels for admitting fluids to said balloons and said separate chamber wherein:

(i) said channels for said fixed distal balloons and separate chamber form an integrated channel for mounting said sliding balloon.

* * * * *